US012633067B2

(12) United States Patent
Brooks Powell et al.

(10) Patent No.: US 12,633,067 B2
(45) Date of Patent: May 19, 2026

(54) EFFECTIVENESS BOOSTING IN THE METAVERSE

(71) Applicant: INTERNATIONAL BUSINESS MACHINES CORPORATION, Armonk, NY (US)

(72) Inventors: Natalie Brooks Powell, Bolingbrook, IL (US); Sarbajit K. Rakshit, Kolkata (IN); Tami Rose Bryan, Howard, MD (US); Zachary A. Silverstein, Georgetown, TX (US)

(73) Assignee: International Business Machines Corporation, Armonk, NY (US)

( * ) Notice: Subject to any disclaimer, the term of this patent is extended or adjusted under 35 U.S.C. 154(b) by 153 days.

(21) Appl. No.: 18/515,870

(22) Filed: Nov. 21, 2023

(65) Prior Publication Data

US 2025/0166314 A1 May 22, 2025

(51) Int. Cl.
| | |
|---|---|
| *G06T 19/00* | (2011.01) |
| *A61B 5/16* | (2006.01) |
| *H04L 67/306* | (2022.01) |

(52) U.S. Cl.
CPC ............ *G06T 19/006* (2013.01); *A61B 5/163* (2017.08); *A61B 5/165* (2013.01); *H04L 67/306* (2013.01)

(58) Field of Classification Search
None
See application file for complete search history.

(56) References Cited

U.S. PATENT DOCUMENTS

| | | | |
|---|---|---|---|
| 9,305,319 | B2 | 4/2016 | Maor |
| 11,475,781 | B2 | 10/2022 | Silverstein |
| 2014/0292637 | A1 * | 10/2014 | Peng .................... G02B 27/017 |
| | | | 345/156 |

(Continued)

OTHER PUBLICATIONS

Disclosed Anonymously, "Dynamic Metaverse Collaborative Environment Creation based on "Last Best Experience" of the Participants," IP.com, Jul. 20, 2022, 5 pages, IP.com No. IPCOM000270584D, Retrieved from the Internet: <URL: https://priorart.ip.com/IPCOM/000270584>.

(Continued)

*Primary Examiner* — Zhengxi Liu
(74) *Attorney, Agent, or Firm* — Kelsey M. Skodje

(57) ABSTRACT

According to at least one embodiment, a method, a computer system, and a computer program product for the metaverse is provided. The present invention may include receiving historical data for one or more participants; creating an attentiveness profile for the participants in a metaverse collaborative session based on the received historical data; segmenting the participants in the session into one or more groups; customizing the session for at least one of the one or more groups; continuously monitoring attentiveness and engagement of at least one of the one or more participants throughout the session; determining whether the attentiveness and engagement of at least one of the participants require boosting; and upon determining that the attentiveness and engagement of at least one of the participants require boosting, dynamically modifying the session to improve the attentiveness and engagement of at least one of the participants whose attentiveness and engagement require boosting.

20 Claims, 3 Drawing Sheets

(56)  References Cited

U.S. PATENT DOCUMENTS

| | | | |
|---|---|---|---|
| 2016/0188181 A1* | 6/2016 | Smith ................. | G06F 3/04886 |
| | | | 715/765 |
| 2018/0024624 A1 | 1/2018 | Gentilin | |
| 2019/0005848 A1* | 1/2019 | Garcia Kilroy ........ | G16H 40/67 |
| 2019/0092337 A1* | 3/2019 | Chua .................... | B60W 30/14 |
| 2021/0082300 A1* | 3/2021 | Silverstein ............. | G06F 3/011 |
| 2023/0078612 A1 | 3/2023 | Tartz | |
| 2024/0427420 A1* | 12/2024 | Harviainen ........ | H04N 21/8456 |
| 2025/0005785 A1* | 1/2025 | Blakeslee .............. | A61B 5/165 |
| 2025/0173516 A1 | 5/2025 | Garcia Delgado et al. | |

OTHER PUBLICATIONS

Disclosed Anonymously, "Focus-of-Interest Immersive Media Multisource Manipulation for a Heightened Virtual Experience," IP.com, Dec. 14, 2022, 5 pages, IP.com No. IPCOM000271439D, Retrieved from the Internet: <URL: https://priorart.ip.com/IPCOM/000271439>.

Sheppard, et al., "Digital eye strain: prevalence, measurement and amelioration," BMJ Open Ophthalmology [review], 2018 [accessed on Oct. 11, 2023], 10 pages, vol. 3, DOI: 10.1136/bmjophth-2018-000146, Retrieved from the Internet: <URL: https://www.ncbi.nlm.nih.gov/pmc/articles/PMC6020759/>.

Witt, "How VR Impacts the Health of Remote Workers and Metaverse Users," Acceleration Economy [My Metaverse Minute], Oct. 25, 2022 [accessed on Oct. 11, 2023], 8 pages, Retrieved from the Internet: <URL: https://accelerationeconomy.com/metaverse/how-vr-impacts-the-health-of-remote-workers-and-metaverse-users/>.

* cited by examiner

100

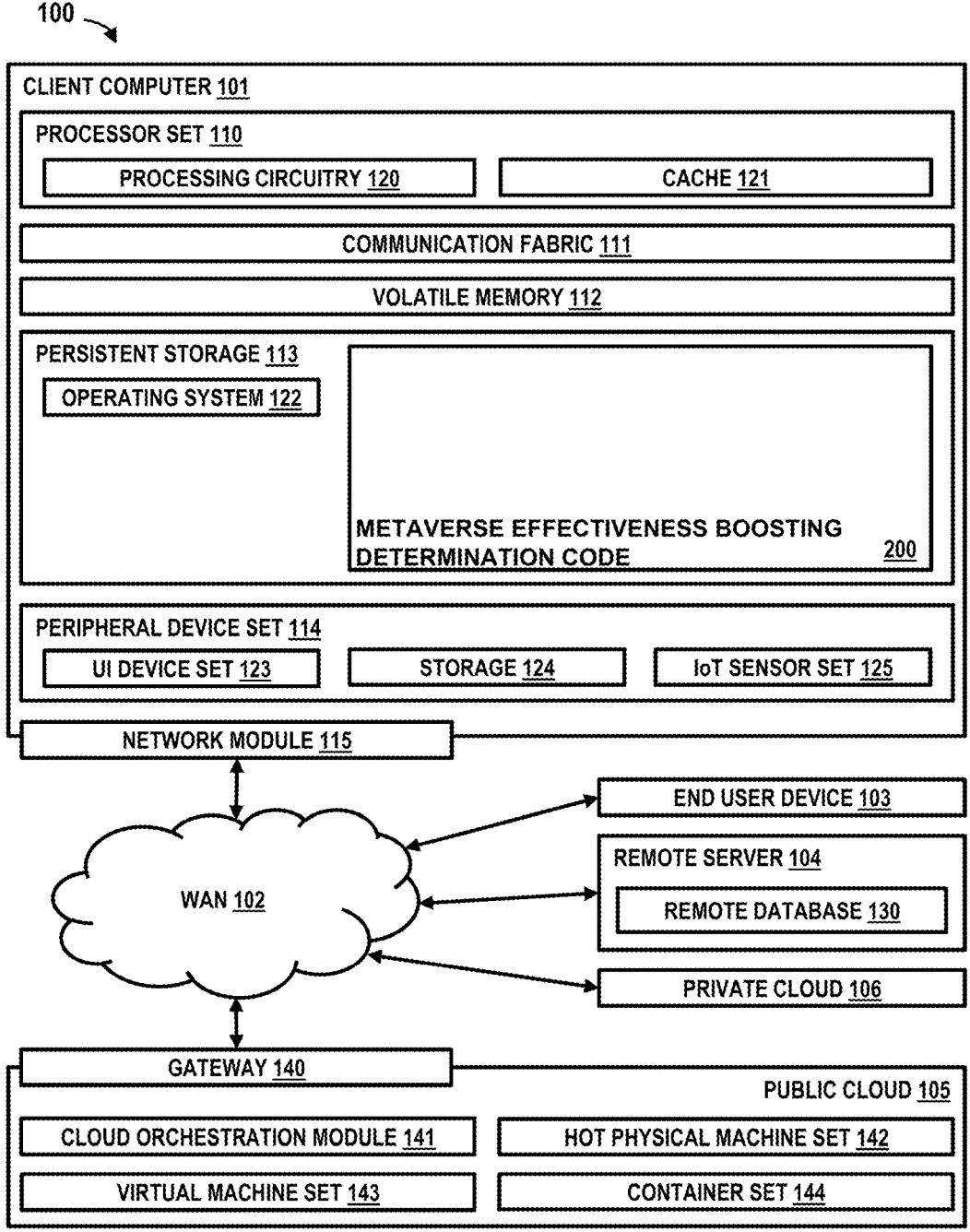

CLIENT COMPUTER 101

PROCESSOR SET 110

PROCESSING CIRCUITRY 120    CACHE 121

COMMUNICATION FABRIC 111

VOLATILE MEMORY 112

PERSISTENT STORAGE 113

OPERATING SYSTEM 122

METAVERSE EFFECTIVENESS BOOSTING DETERMINATION CODE    200

PERIPHERAL DEVICE SET 114

UI DEVICE SET 123    STORAGE 124    IoT SENSOR SET 125

NETWORK MODULE 115

WAN 102

END USER DEVICE 103

REMOTE SERVER 104

REMOTE DATABASE 130

PRIVATE CLOUD 106

GATEWAY 140

PUBLIC CLOUD 105

CLOUD ORCHESTRATION MODULE 141    HOT PHYSICAL MACHINE SET 142

VIRTUAL MACHINE SET 143    CONTAINER SET 144

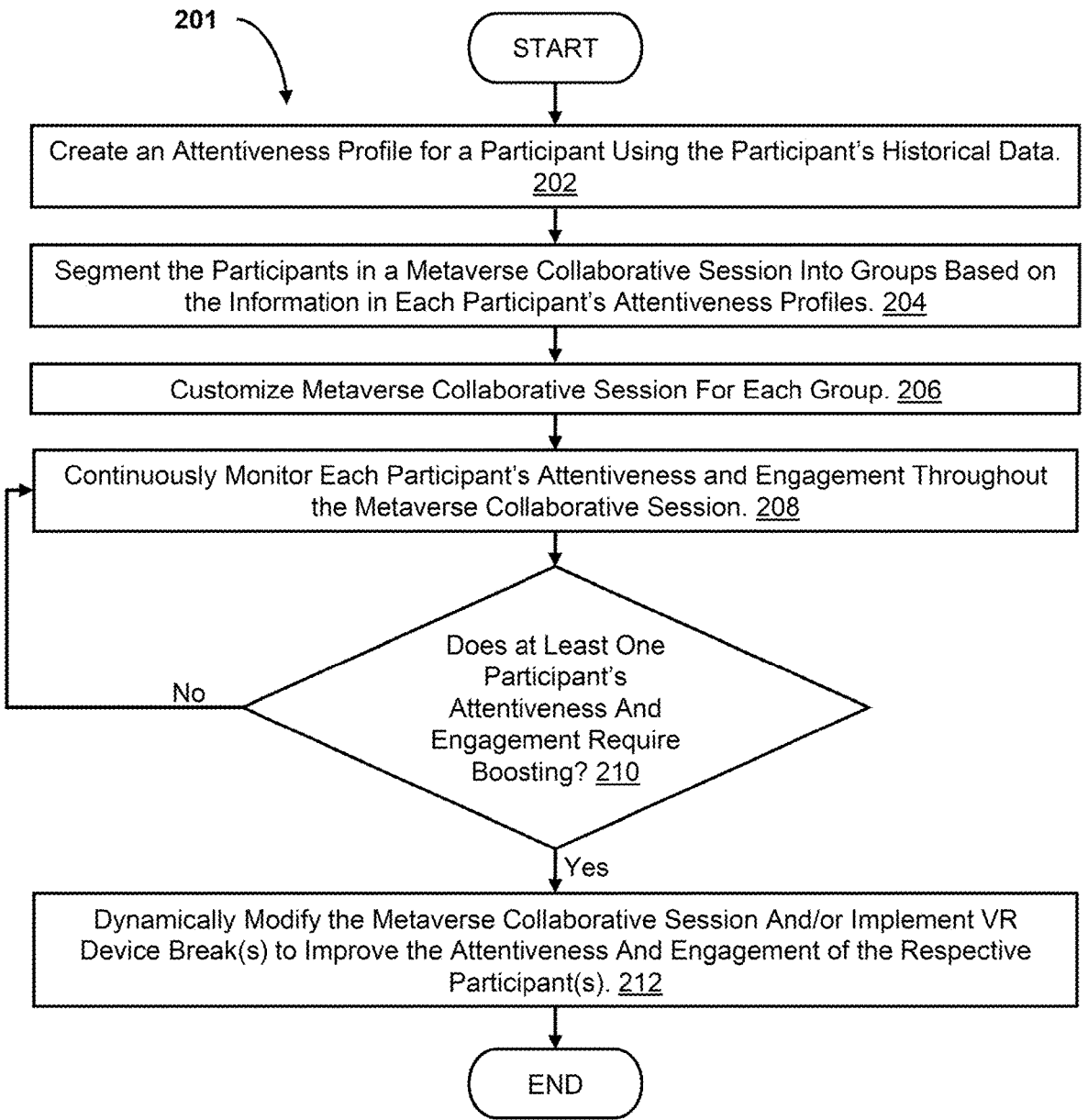

START

Create an Attentiveness Profile for a Participant Using the Participant's Historical Data. 202

Segment the Participants in a Metaverse Collaborative Session Into Groups Based on the Information in Each Participant's Attentiveness Profiles. 204

Customize Metaverse Collaborative Session For Each Group. 206

Continuously Monitor Each Participant's Attentiveness and Engagement Throughout the Metaverse Collaborative Session. 208

Does at Least One Participant's Attentiveness And Engagement Require Boosting? 210

No

Yes

Dynamically Modify the Metaverse Collaborative Session And/or Implement VR Device Break(s) to Improve the Attentiveness And Engagement of the Respective Participant(s). 212

END

FIGURE 2

EFFECTIVENESS BOOSTING IN THE METAVERSE

BACKGROUND

The present invention relates generally to the fields of artificial intelligence, virtual reality ("VR"), and augmented reality ("AR"), and, in particular, to the metaverse.

The metaverse is a hypothetical iteration of the internet as a single, universal, and immersive virtual world. The metaverse is built on the convergence of virtual reality and augmented reality, which allows for a web of networked immersive experiences in multiuser persistent platforms. Collaborations can occur in the metaverse where participants can together engage with virtual content, such as learning activities, in ways in which physical limitations are transcended.

SUMMARY

Embodiments of a method, a computer system, and a computer program product for the metaverse are described. According to one embodiment of the present invention, a method, computer system, and computer program product for the metaverse may include receiving historical data for one or more participants; creating an attentiveness profile for the participants in a metaverse collaborative session based on the received historical data of the participants; segmenting the participants in the metaverse collaborative session into one or more groups based on information in each participant's attentiveness profile; customizing the metaverse collaborative session for at least one of the one or more groups; continuously monitoring an attentiveness and engagement of at least one of the one or more participants throughout the metaverse collaborative session; determining whether the attentiveness and engagement of at least one of the participants require boosting; and upon determining that the attentiveness and engagement of at least one of the participants require boosting, dynamically modifying the metaverse collaborative session to improve the attentiveness and engagement of at least one of the participants whose attentiveness and engagement require boosting.

BRIEF DESCRIPTION OF THE SEVERAL VIEWS OF THE DRAWINGS

These and other objects, features, and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 1 illustrates an exemplary networked computer environment according to at least one embodiment.

FIG. 2 is an operational flowchart illustrating a metaverse effectiveness boosting determination process according to at least one embodiment.

DETAILED DESCRIPTION

Figure 3:
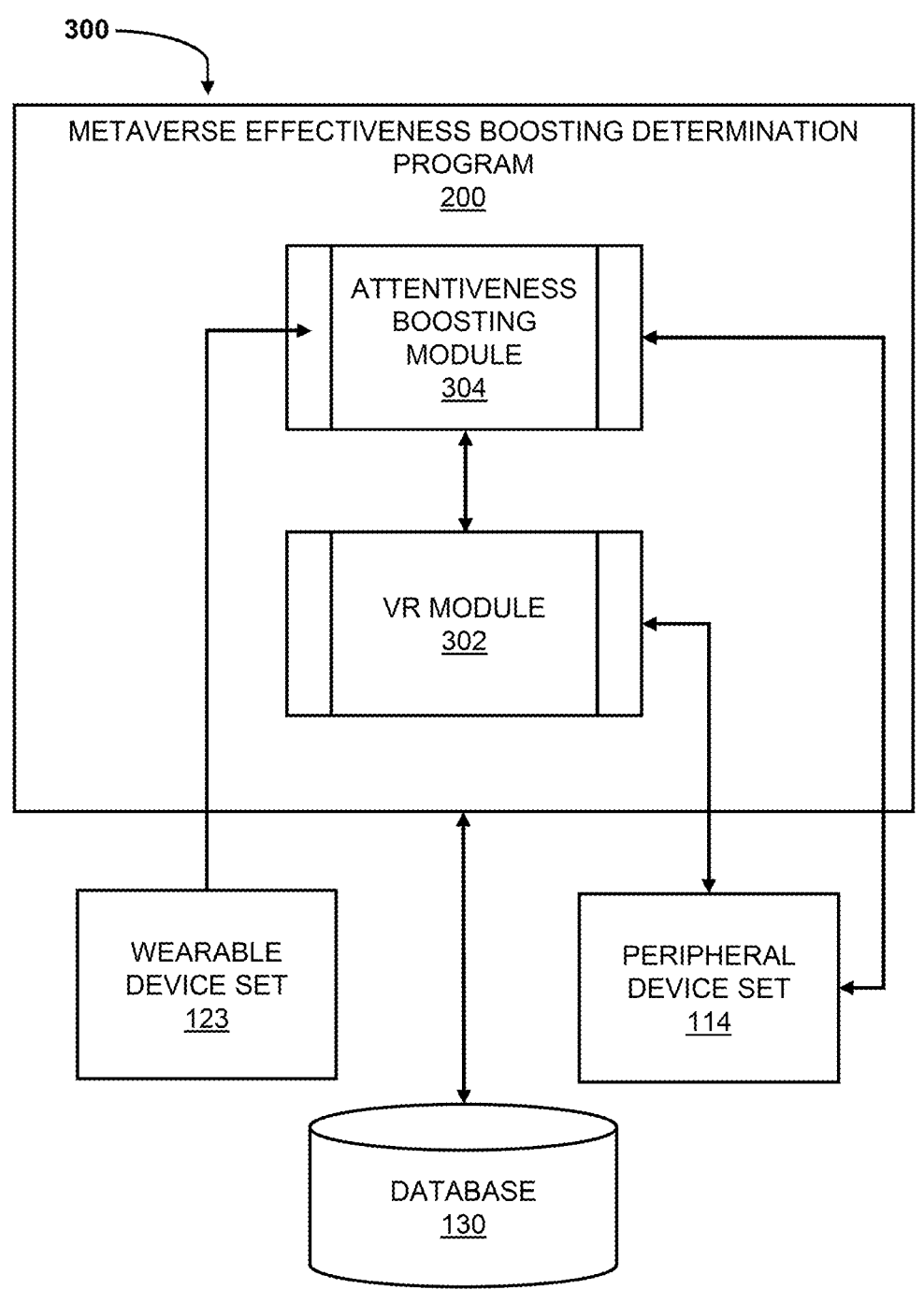
FIG. 3 is a system diagram illustrating an exemplary program environment of an implementation of a metaverse effectiveness boosting determination process according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Embodiments of the present invention relate to the fields of artificial intelligence, virtual reality ("VR"), and augmented reality ("AR"), and more particularly to the metaverse. The following described exemplary embodiments provide a method, program product, and system to, among other things, dynamically maintain the participants in a metaverse collaborative session's threshold levels of attentiveness and engagement throughout the session. Therefore, according to an aspect of the invention, the present embodiment has the capacity to improve collaborative sessions in the metaverse by predicting if and when the participants' attentiveness and engagement will decline during a metaverse collaborative session. In response, aspects of the metaverse collaborative session can be customized based on any predicted decline. The real-time attentiveness and engagement of the participants throughout the metaverse collaboration session are monitored and modified. Based on the monitoring of the participants, the metaverse collaborative session is modified.

As previously described, the metaverse is a hypothetical iteration of the internet as a single, universal, and immersive virtual world. The metaverse is built on the convergence of virtual reality and augmented reality, which allows for a web of networked immersive experiences in multiuser persistent platforms. Collaborations can occur in the metaverse where participants can together engage with virtual content, such as learning activities, in ways in which physical limitations are transcended. However, collaborations in the metaverse can lead to monotony as well as eye fatigue. Monotonous activities, i.e., activities that are dull, tedious, repetitious, and lacking in variety and interest, can lead to the participants becoming less engaged and attentive. Additionally, prolonged wearing of a virtual reality device ("VR device") can lead to the onset of various types of eye fatigue, such as eye strain and/or motion sickness. Vergence-accommodation conflict is a visual phenomenon that occurs when the brain receives mismatching cues between vergence and accommodation of the eye. Current methods attempt to increase engagement and attentiveness among participants in virtual collaborations by implementing distraction reduction methods, such as adjusting the characteristics of virtual content in a simulated environment. However, these distraction reduction methods are implemented at the initiation of a virtual collaboration session and thus, do not actively monitor and dynamically manage the participants' attentiveness and engagement. Additionally, current methods attempt to reduce the onset of eye fatigue by recommending participants take regular breaks, from using their VR devices, in compliance with manufacturer guidelines, to rest their eyes and avoid prolonged continuous use. However, eye fatigue can occur at different durations of VR device use for each participant. Thus, the recommendation of taking regular breaks may not be effective in avoiding eye fatigue for all participants in a virtual collaborative session. Therefore, it may be likely that the attentiveness and engagement of participants in a metaverse collaborative session is unknowingly low at varying points throughout the session, and as a result, successful collaboration between participants in the metaverse is not occurring.

Thus, embodiments of the present invention may provide advantages, as explained in the subsequent paragraphs, including, but not limited to, increasing the number and frequency of successful collaborations in the metaverse between groups of participants. The present invention can dynamically maintain the participants in a metaverse collaborative session's threshold levels of attentiveness and engagement throughout the session by predicting the decline of a participant's attentiveness and engagement based on the prediction results, customizing the metaverse collaborative session. Modifications to the metaverse collaborative session can be dynamically implemented. Additionally, VR device breaks can be recommended based on the continuous monitoring of the attentiveness and engagement of the participants throughout the session. The present invention does not require that all advantages need to be incorporated into every embodiment of the invention.

According to at least one other embodiment, the program can create an attentiveness profile for a participant. The attentiveness profile may comprise attentiveness and engagement characteristics, such as physiological responses, including but not limited to a participant's heart rate, electrodermal activity, electroencephalography ("EEG"), eye tracking, respiration rate, blood pressure, etc., and behavioral responses, including but not limited to the participant's head movements, gaze direction, interactions with virtual objects, participant response times, eye movement patterns, fixation duration, pupil dilation, voice and speech analysis, etc. The attentiveness profile further comprises historical information related to the participant that contributed to the participant's attention and engagement during their previously attended metaverse collaborative session(s). The historical information includes the type(s) of metaverse collaborative session that the participant has previously attended, the contents of the session(s), factors that contributed to the participant's reduced attentiveness/engagement, the types of visuals displayed during a session, the form of content delivery, the frequency and duration of the participant's participation in a session, information representing the participant's eye fatigue/strain during a session, health conditions, contextual scenarios, participant feedback on the collaborative session, wearable device feed analysis, etc. The program uses the various sensors and technologies integrated into the VR device to capture and collect data during each metaverse collaborative session that the participant attends, such as eye-tracking devices, motion sensors, and EEG headsets. Additionally, the program uses various sensors in a wearable device, such as a smartwatch, to record a participant's biometric data and convert it into a digital format. A participant may comprise a VR device wearer, as well as a wearable device wearer in combination with wearing the VR device, who is participating in a metaverse collaborative session. The program can analyze the data by applying signal processing techniques, such as Moving Average, Gaussian, or Kalman filters, machine learning algorithms, such as classifications algorithms or regression algorithms, and/or statistical analysis methods, such as descriptive statistics or inferential statistics, to derive attention and engagement characteristics. For example, attention and engagement characteristics may be derived by applying a set of attention metrics that can quantify the participant's engagement and attentiveness levels. The program can store the attentiveness profiles in the database by saving the profiles in files.

According to at least one embodiment, the attentiveness profile can additionally comprise a participant's predetermined attentiveness and engagement threshold limits. The threshold limits can represent the program's predictions of the lowest levels of the quantified attentiveness and engagement characteristics at which the participant is still paying optimal attentiveness and engagement in a metaverse collaborative session, i.e., how long a participant can attend a future metaverse collaborative session until the participant has likely experienced a decrease in their attentiveness and engagement indicating that the participant's attention has been drastically or completely lost. For example, the program may calculate an abandonment score for a participant, which can represent the program's predictions of the duration of time until a participant leaves a metaverse collaborative session based on their attentiveness and engagement at/in the metaverse collaborative session. The program can calculate attentiveness and engagement threshold limits using a trained predictive model.

According to at least one embodiment, the program can train machine learning models and/or statistical modeling techniques to develop a predictive model based on the historical data of the participants. The trained model, such as an Adaptive Bayesian Neural Network ("BNN"), can output optimal durations for future metaverse collaborative sessions, predicted attentiveness and engagement levels of a participant, the significance of attentiveness and engagement characteristics in maintaining a participant's attentiveness and engagement levels above their respective threshold levels throughout a metaverse collaborative session, and modifications to a metaverse collaborative session that can improve the attentiveness and engagement levels of the participant, such as the number of breaks during each session for the participant, alternate consumption manners, content modifications, visual cues, audio effects, and interactive elements to implement into the metaverse simulated environment. The program can train the model using a participant's collected historical data. The program can assign weights to different attentiveness and engagement characteristics based on their determined significance in maintaining a participant's attentiveness and engagement levels above their respective threshold levels throughout a metaverse collaborative session. The trained model can continuously learn and update its posterior distribution over the weights of characteristics as new data is introduced.

According to at least one embodiment, the participants in the metaverse collaborative session can be segmented into one or more groups based on the plurality of participants having similarities in their attentiveness profiles. The program can segment the participants into groups based on the information in their attentiveness profiles. For example, the program can cluster groups based on similarities in the participants' threshold levels of attentiveness and engagement. The program can segment participants into groups using unsupervised learning techniques, such as clustering algorithms.

According to at least one embodiment, the metaverse collaborative session can be customized for at least one of the one or more groups of participants. The program can customize a metaverse collaborative session based on the information in the attentiveness profiles of the participants in a group, such as the averaged attentiveness and engagement threshold levels of the participants. For example, the program can redesign a metaverse collaborative session in a way that maximizes the outcomes of the session for each group, such as by alternating the methods of consumption for the content in the session, varying the agenda of the session, modifying the contents of the session, modifying the visuals and interactive elements in the metaverse simulated environment, etc.

According to at least one embodiment, the attentiveness and engagement of at least one of the one or more participants in the metaverse collaborative session can be continuously monitored throughout the metaverse collaborative session. The program can continuously monitor the attentiveness and engagement of the participants by dynamically analyzing the captured attentiveness and engagement characteristics of the participants using the trained model. The program can continuously receive data from the VR devices and wearable devices and can feed the data into the trained model as the data is collected. The program can continuously update the real-time attentiveness and engagement levels of the participants in real-time based on the outputted results from the trained predictive model.

According to at least one embodiment, whether the attentiveness and engagement of at least one of the one or more participants require boosting can be determined upon the detection that one or more of the attentiveness and engagement levels of a participant have decreased below the participant's threshold levels. The program may detect that the attentiveness or engagement levels of a participant require boosting by dynamically comparing the current attentiveness and engagement levels of the participant to their attentiveness and engagement threshold levels comprised within their attentiveness profiles. As previously stated, the program can dynamically compute the real-time attentiveness and engagement levels of each participant throughout the metaverse collaborative session using the trained predictive model. Once the model generates the participant's real-time attentiveness and engagement levels, the program can compare the real-time levels to the respective participant's attentiveness and engagement threshold levels. Specifically, the program can detect that a participant's attentiveness and engagement require boosting upon the latest attentiveness and engagement threshold level comparison validating that one or more of the participant's attentiveness and engagement levels have fallen below one or more of their respective predetermined attentiveness and engagement threshold levels.

According to at least one other embodiment, the program can identify that a participant is experiencing a loss of attentiveness and engagement due to eye fatigue using the trained predictive model. The program can determine eye fatigue by analyzing a participant's eye strain, changes in the participant's pupil size, blink frequency, eye movements, head orientation, fixation duration, and pupil dilation, using the trained predictive model throughout the metaverse collaborative session.

According to at least one embodiment, in response to determining that the attentiveness and engagement levels of at least one of the one or more participants require boosting, the program can dynamically modify the metaverse collaborative session accordingly to improve the attentiveness and engagement of the one or more participants. The program can create and insert visualizations/visual cues, such as 3D effects, audio effects, interactive elements, and 4D effects, such as haptic feedback or any other sensory stimuli, into the metaverse simulated environment. Also, the program can adjust content in the session, such as the visuals and sound effects in the metaverse simulated environment. Additionally, the program may prompt interactions between participants. The program can determine if the implemented modifications to the metaverse collaborative session are improving the attentiveness and engagement levels of a participant based on the utilized feedback loop.

According to at least one other embodiment, in response to detecting that one or more participants are experiencing a loss of attentiveness and engagement due to eye fatigue, a virtual reality device break for the one or more participants may be implemented. The program can implement a VR device break by pausing the metaverse collaborative session for a predetermined amount of time and instructing the participants to remove their VR devices via a prompt on the GUI of the VR device.

According to at least one other embodiment, the one or more participants may be inserted into the metaverse collaborative session by displaying a metaverse simulated environment on the participants' VR devices. A metaverse collaborative session may comprise one or more participants, such as a teacher and students, meeting in a metaverse simulation, such as a virtual classroom.

The present invention may be a system, a method, and/or a computer program product at any possible technical detail level of integration. The computer program product may include a computer-readable storage medium (or media) having computer-readable program instructions thereon for causing a processor to carry out aspects of the present invention.

Various aspects of the present disclosure are described by narrative text, flowcharts, block diagrams of computer systems, and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer-readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer-readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation, or garbage collection, but this does not render the storage device as transitory because the data is not transitory while it is stored.

The following described exemplary embodiments provide a system, method, and program product for the metaverse, comprising receiving historical data for one or more participants, creating an attentiveness profile for the participants in a metaverse collaborative session based on the received historical data of the participants, segmenting the participants in the metaverse collaborative session into one or more groups based on information in each participant's attentiveness profile, customizing the metaverse collaborative session for at least one of the one or more groups, continuously monitoring an attentiveness and engagement of at least one of the one or more participants throughout the metaverse collaborative session, determining whether the attentiveness and engagement of at least one of the participants require boosting, and upon determining that the attentiveness and engagement of at least one of the participants require boosting, dynamically modifying the metaverse collaborative session to improve the attentiveness and engagement of at least one of the participants whose attentiveness and engagement require boosting.

Beginning now with FIG. 1, an exemplary networked computer environment 100 is depicted, according to at least one embodiment. Computing environment 100 contains an example of an environment for the execution of at least some of the computer code involved in performing the inventive methods, such as metaverse effectiveness boosting determination code 200, also referred to as metaverse effectiveness boosting determination program 200, and "the program" 200. In addition to code block 200 computing environment 100 includes, for example, computer 101, wide area network (WAN) 102, end-user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and code block 200, as identified above), peripheral device set 114 (including user interface (UI), device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smartphone, smartwatch or other wearable computer, mainframe computer, quantum computer, or any other form of computer or mobile device now known or to be developed in the future that is capable of running an algorithm, accessing a network or querying a database, such as remote database 130. Database 130 may comprise a knowledge corpus. The knowledge corpus may comprise trained machine learning models, such as a trained Adaptive Bayesian Neural Network, natural language processing algorithms, and statistical modeling techniques. The knowledge corpus may comprise training data used to train the models, such as collected historical data on participants' past metaverse collaborative sessions. Additionally, the knowledge corpus may comprise data on digital visuals and mixed reality simulated environments. The database 130 may comprise participants' attentiveness profiles as well as information comprised within the profiles. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off-chip." In some computing environments, processor set 110 may be designed for working with qubits and performing quantum computing.

Computer-readable program instructions are typically loaded onto computer 101 to cause a series of operational steps to be performed by processor set 110 of computer 101 and thereby affect a computer-implemented method, such that the instructions thus executed will instantiate the methods specified in flowcharts and/or narrative descriptions of computer-implemented methods included in this document (collectively referred to as "the inventive methods"). These computer-readable program instructions are stored in various types of computer-readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in code block 200 in persistent storage 113.

COMMUNICATION FABRIC 111 is the signal conduction path that allows the various components of computer 101 to communicate with each other. Typically, this fabric is made of switches and electrically conductive paths, such as the switches and electrically conductive paths that make up buses, bridges, physical input/output ports, and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read-only memory (ROM), but typically at least a portion of the persistent storage allows writing of data, deletion of data, and re-writing of data. Some familiar forms of persistent storage include magnetic disks and solid-state storage devices. Operating system 122 may take several forms, such as various known proprietary operating systems or open-source Portable Operating System Interface type operating systems that employ a kernel. The code included in code block 200 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made through local area communication networks and even connections made through wide area networks such as the internet. In various embodiments, UI device set 123 may include components such as a display screen, speaker, microphone, wearable devices (such as goggles and smartwatches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector. Additionally, peripheral device set 114 may comprise a virtual reality (VR) device 114, also referred to as a "VR device" 114.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer-readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as application-specific integrated circuits ("ASICs"), copper transmission cables, optical transmission fibers, wireless transmission, routers, firewalls, switches, gateway computers, and edge servers.

END USER DEVICE (EUD) 103 is any computer system that is used and controlled by an end user (for example, a customer of an enterprise that operates computer 101) and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as a thin client, heavy client, mainframe computer, desktop computer, and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs, and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community, or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

According to the present embodiment, the metaverse effectiveness boosting determination program 200, may be a program capable of creating an attentiveness profile for a participant using the participant's historical data, continuously monitoring each participant's attentiveness and engagement throughout the metaverse collaborative session, determining whether the attentiveness and engagement of one or more of the participants require boosting, and upon determining that the attentiveness and engagement of one or more of the participants require boosting, dynamically modifying the metaverse collaborative session and/or recommending a VR device break 114 to improve the attentiveness and engagement of the respective participants. The program 200 may be located on client computing device 101 or remote server 104 or on any other device located within network 102. Furthermore, the program 200 may be distributed in its operation over multiple devices, such as client computing device 101 and remote server 104. The metaverse effectiveness boosting determination method is explained in further detail below with respect to FIG. 2.

FIG. 2 is an operational flowchart illustrating a metaverse effectiveness boosting determination process 201 according to at least one embodiment. At 202, the program 200 creates an attentiveness profile for a participant using the participant's historical data. As previously stated, the attentiveness profile may comprise attentiveness and engagement characteristics, such as physiological responses, including, but not limited to a participant's heart rate, electrodermal activity, electroencephalography ("EEG"), eye tracking, respiration rate, blood pressure, etc., and behavioral responses, including, but not limited to the participant's head movements, gaze direction, interactions with virtual objects, participant response times, eye movement patterns, fixation duration, pupil dilation, voice and speech analysis, etc. The attentiveness profile may further comprise historical information related to the participant that contributed to the participant's attention and engagement during their previously attended metaverse collaborative session(s). The historical information may include the types of metaverse collaborative sessions that the participant has previously attended (e.g., a casual hang out, educational class, business meeting, or a social gathering), the contents of the sessions (e.g., the content discussed/presented at a session), factors that contributed to the participant's reduced attentiveness/engagement (e.g., repetitive content or lack of interactivity), the types of visuals displayed during a session (e.g., virtual graphs or 3D images, the form of content delivery, e.g., through video, spoken voice, or interactive virtual elements), the frequency and duration of the participant's participation in a session, information representing the participant's eye fatigue during a session (e.g., pupil size, blink frequency, and eye movements of the participants), health conditions (e.g., the participant's reported discomfort or health limitations), contextual scenarios (e.g., the time of day in which the metaverse collaborative session is occurring or the complexity of the presented content), participant feedback on the collaborative session (e.g., points during the session in which the participant experienced boredom), and wearable device feed analysis (e.g., the participant's heart rate).

The program 200 can use various sensors and technologies integrated into the VR device 114 to capture and collect data during each metaverse collaborative session that the participant attends, such as eye-tracking devices, motion sensors, and EEG headsets. Additionally, the program 200 may use various sensors in a wearable device 123, such as a smartwatch, to record a participant's biometric data and convert it into a digital format. A participant may comprise a VR device 114 wearer, as well as a wearable device 123 wearer in combination with wearing the VR device 114, who is participating in a metaverse collaborative session. The program 200 can analyze the data by applying signal processing techniques, such as Moving Average, Gaussian, or Kalman filters, machine learning algorithms, such as classifications algorithms or regression algorithms, and/or statistical analysis methods, such as descriptive statistics or inferential statistics, to derive attention and engagement characteristics. For example, attention and engagement characteristics may be derived by applying a set of attention metrics that can quantify the participant's engagement and attentiveness levels. The program 200 can store the attentiveness profiles in the database 130 by saving the profiles in files.

As previously stated, a metaverse collaborative session may comprise one or more participants, such as a teacher and students, meeting in a metaverse simulated environment, such as a virtual classroom. The program 200 can create a metaverse collaborative session comprising a virtual simulated environment and virtual objects. The program 200 can render virtual objects and a virtual simulated environment via the VR module 302 (FIG. 3) of the virtual reality device 114. The program 200 may feed data representing a virtual simulated environment and virtual objects to the VR device 114. The virtual simulated environment may comprise virtual elements. The virtual simulated environment may comprise a virtual world in which one or more VR device 114 wearers may enter, see, move around in, interact with, etc. through the medium of a VR device 114. The VR device 114 wearers in the virtual simulated environment may be able to see and/or interact with the same virtual objects and virtual elements and may interact with virtual representations of each other. The virtual simulated environment may comprise VR environments such as generated images, sounds, haptic feedback, and other sensations. Additionally, the virtual simulated environment may comprise virtual simulated environments that fully replace a physical environment with virtual elements, such that a VR device 114 wearer experiencing a virtual simulated environment cannot see any objects or elements of the physical world; however, the virtual simulated environments are anchored to real-world locations, such that the movement of the VR device 114 wearers, virtual objects, virtual environmental effects and elements all occur relative to the corresponding locations in the physical environment.

A VR device 114 may be any device or combination of devices, such as a headset, enabled to record world information that the VR module 302 (FIG. 3) may overlay with computer-generated perceptual elements to create a metaverse simulated environment. The VR device(s) 114 can record the actions, position, movements, etc. of a VR device 114 wearer, to track the VR device 114 wearer's movement within and interactions with the VR environment. The VR device 114 can display a virtual simulated environment to a VR device 114 wearer, allowing the VR device 114 wearer to interact with the VR environment. Also, the VR device 114 can comprise a head-mounted display ("HMD"). Additionally, the VR device 114 may be equipped with or comprise a number of sensors, such as a camera, microphone, and accelerometer, and these sensors may be equipped with or comprise a number of user interface devices such as touchscreens, speakers, etc.

Additionally, the attentiveness profile can comprise a participant's predetermined attentiveness and engagement threshold limits. The threshold limits can represent the program's 200 predictions of the lowest levels of the quantified attentiveness and engagement characteristics at which the participant is still paying optimal attentiveness and engagement in a metaverse collaborative session, i.e., how long a participant can attend a future metaverse collaborative session until the participant has likely experienced a decrease in their attentiveness and engagement indicating that the participant's attention has been drastically or completely lost. For example, the program 200 may calculate an abandonment score for a participant, which can represent the program's 200 predictions of the duration of time until a participant leaves a metaverse collaborative session based on their attentiveness and engagement at/in the metaverse collaborative session. The program 200 can calculate attentiveness and engagement threshold limits using a trained predictive model. One example of an attentiveness and engagement threshold limit may be calculated based on the total number of interactions of the participant in a metaverse collaborative session. A rating can comprise a number from zero (0) through five (5), with zero (0) indicating a metaverse collaborative session that is least desired by the participant, and five (5) indicating a metaverse collaborative session that is most desired by the participant.

The program 200 can train machine learning models and/or statistical modeling techniques to develop a predictive model based on the historical data of the participants. The trained model, such as an Adaptive Bayesian Neural Network ("BNN"), can output optimal durations for future metaverse collaborative sessions, predicted attentiveness and engagement levels of a participant, the significance of attentiveness and engagement characteristics in maintaining a participant's attentiveness and engagement levels above their respective threshold levels throughout a metaverse collaborative session, and modifications to a metaverse collaborative session that can improve the attentiveness and engagement levels of the participant, such as the number of breaks during each session for the participant, alternate consumption manners, content modifications, visual cues, audio effects, and interactive elements to implement into the metaverse simulated environment. The program 200 can train the model using a participant's collected historical data. The program 200 can assign weights to different attentiveness and engagement characteristics based on their determined significance in maintaining a participant's attentiveness and engagement levels above their respective threshold levels throughout a metaverse collaborative session. The trained model can continuously learn and update its posterior distribution over the weights of characteristics as new data is introduced.

The program 200 can analyze eye strain/fatigue experienced by the participant during previous metaverse collaborative sessions. As previously stated, the program 200 can determine eye strain/fatigue by analyzing factors indicative of visual fatigue and strain, such as changes in pupil size, blink frequency, eye movements, head orientation, fixation duration, or pupil dilation during metaverse collaborative sessions. The program 200 can capture pupil size, blink frequency, and eye movements using a VR device's 114 headset camera. The program 200 can use image recognition to analyze the data captured by the VR device 114 camera to determine pupil size, blink frequency, and eye movements, of the participant. Additionally, the program 200 can analyze the eye strain experienced by the participant to identify correlations between the patterns and factors such as screen time, display quality, and reported eye strain.

In some embodiments, if historical data does not exist for a participant, the program 200 may determine the attentiveness and engagement limits for the participant using the Attention Control Scale. The Attention Control Scale can be a self-report scale that can measure two major components of attention, attention focusing and attention shifting. The attention control can consist of twenty items that are rated on a four-point Likert scale from 1 (one), almost never, to four (4), always. The program 200 can administer the Attention Control Scale to a participant before the initiation of a metaverse collaborative session. The program 200 may assign attentiveness and engagement threshold limits to a participant based on the participant's responses to the Attention Control Scale. For example, the program 200 may determine that the closer a participant is to a score of twenty (20), the more likely the participant is to lose their attention and/or become disengaged in the session.

At 204, the program 200 segments the participants in a metaverse collaborative session into groups based on the participants' attentiveness profiles. The program 200 can segment the participants in the metaverse collaborative session into one or more groups based on the plurality of participants having similarities in their attentiveness profiles. The program 200 can segment the participants into groups based on the information in their attentiveness profiles. For example, the program 200 may cluster groups based on similarities in the participants' threshold levels of attentiveness and engagement. The program 200 can segment participants into groups using unsupervised learning techniques, such as clustering algorithms. A detailed example may entail a metaverse collaborative session that comprises twenty (20) participants in a movie theatre metaverse simulated environment. Four (4) participants comprise an attentiveness profile indicating very low attentiveness/ engagement threshold limits, seven (7) participants comprise an attentiveness profile indicating low attentiveness/ engagement threshold limits, four (4) participants comprise an attentiveness profile indicating medium attentiveness/ engagement threshold limits, and five (5) participants grouped comprise an attentiveness profile indicating high attentiveness/engagement threshold limits. Thus, the program 200 can classify the four (4) participants with very low attentiveness/engagement threshold limits, into one group, for example, group A, the seven (7) participants with low attentiveness/engagement threshold limits into group B, the four (4) participants with medium attentiveness/engagement threshold limits into group C, and the five (5) participants with high attentiveness/engagement threshold limits into group D.

At 206, the program 200 customizes the metaverse collaborative session for each group of participants. As previously stated, the program 200 can customize the metaverse collaborative session for each group of participants based on the information in the attentiveness profiles of the participants in a group, such as the averaged attentiveness and engagement threshold levels of the participants. For example, the program 200 can redesign a metaverse collaborative session in a way that maximizes the outcomes of the session for each group, such as by alternating the methods of consumption for the content in the session, varying the agenda of the session, modifying the contents of the session, modifying the visuals and interactive elements in the metaverse simulated environment, implementing a different number of VR device 114 breaks, shortening/lengthening the content of the session, encouraging direct interactions between participants, etc. The program 200 can onboard each participant group to their redesigned metaverse collaborative session, comprising different presentations/experiences of the same metaverse collaborative session. The program 200 can insert the one or more participants into the metaverse collaborative session by displaying a virtual simulated environment on the participants' VR devices 114.

At 208, the program 200 continuously monitors each participant's attentiveness and engagement throughout the metaverse collaborative session. As previously stated, the program 200 can continuously monitor the attentiveness and engagement of the participants by dynamically analyzing the captured attentiveness and engagement characteristics of the participants using the trained model, much in the same way as performed in step 202 to collect and analyze the historical data of a participant. For example, the program 200 can monitor the eye strain of a participant and determine that the participant is experiencing a loss of attentiveness and engagement due to eye fatigue, based on measuring the real-time blink frequency of the participant is ten percent (10%) lower than their predetermined blink frequency threshold limit by comparing the real-time measured blink frequency to the predetermined blink frequency threshold limit of the participant (e.g., a baseline of fifteen (15) to twenty (20) times per minute). The program 200 can continuously receive data from the VR devices 114 and wearable devices 123 and can feed the data into the trained model as the data is collected. The program 200 can continuously update the real-time attentiveness and engagement levels of the participants in real-time based on the outputted results from the trained predictive model.

At 210, the program 200 determines whether the attentiveness and engagement of at least one of the one or more participants require boosting. According to one implementation, in response to determining that the attentiveness and engagement of at least one of the one or more participants require boosting (step 210, "YES" branch), the program 200 may continue to step 212 to dynamically modify the metaverse collaborative session and/or recommends VR device

114 break(s) to improve the attentiveness and engagement of the respective one or more participants. The program 200 may determine that the attentiveness and engagement of at least one of the one or more participants require boosting, in real-time, upon the detection that one or more of the attentiveness and engagement levels of a participant have decreased below the participant's threshold levels. The program 200 may detect that the attentiveness or engagement levels of a participant require boosting by dynamically comparing the current attentiveness and engagement levels of the participant to their attentiveness and engagement threshold levels comprised within their attentiveness profiles. As previously stated, the program 200 can dynamically compute the real-time attentiveness and engagement levels of each participant throughout the metaverse collaborative session using the trained predictive model. Once the model generates the participant's real-time attentiveness and engagement levels, the program 200 can compare the real-time levels to the respective participant's attentiveness and engagement threshold levels. Specifically, the program 200 can detect that a participant's attentiveness and engagement require boosting upon the latest attentiveness and engagement threshold level comparison validating that one or more of the participant's attentiveness and engagement levels have fallen below one or more of their respective predetermined attentiveness and engagement threshold levels. In response to determining that the attentiveness and engagement of no participants require boosting (step 210, "NO" branch), the program 200 may continue to monitor each participant's attentiveness and engagement throughout the metaverse collaborative session as in Step 208.

In some embodiments, the program 200 may identify that a participant is experiencing a loss of attentiveness and engagement due to eye fatigue using the trained predictive model. The program 200 can determine eye fatigue by analyzing a participant's eye strain, changes in the participant's pupil size, blink frequency, eye movements, head orientation, fixation duration, and pupil dilation, using the trained predictive model throughout the metaverse collaborative session.

In some embodiments, the program 200 may utilize a feedback loop to determine the real-time attentiveness and engagement levels of the participants. For example, the program 200 may display virtual objects and based on the participant's engagement with the objects, determine an increase in the attentiveness and engagement of the participant. Alternatively, the program 200 may determine a decrease in the attentiveness and engagement of the participant based on the participant's lack of engagement with the objects. The participants can interact with virtual objects via the GUI of their VR device 114. Additionally, for example, the program 200 can determine the real-time attentiveness and engagement levels of each participant through questions asked in a discussion session, participation in polls, surveys, games, and trivia, and can provide the participant a score out of the total possible interactions. Scores, for example, below fifty percent (50%) can indicate the need for attention/ engagement boosting. For example, if there were a total of twelve (12) activities in a collaborative session, such as six (6) questions asked, three (3) polls, two (2) surveys, and one (1) game, and the participant answered three (3) questions, and two (2) polls, the program 200 may determine that the attentiveness and engagement levels of the participant require boosting.

At 212, the program 200 dynamically modifies the metaverse collaborative session and/or implements VR device 114 break(s) to improve the attentiveness and engagement of the respective one or more participants. As previously stated, in response to determining that the attentiveness and engagement levels of at least one of the one or more participants require boosting, the program 200 can dynamically modify the metaverse collaborative session accordingly to improve the attentiveness and engagement of the one or more participants. The program 200 can modify the metaverse collaborative session by dynamically creating and inserting visualizations/visual cues, such as 3D effects, audio effects, interactive elements, and 4D effects, such as haptic feedback, i.e., causing the VR device 114 to vibrate, or any other sensory stimuli, into the metaverse simulated environment. Also, the program 200 may adjust content in the session, such as the visuals and sound effects in the metaverse simulated environment. Additionally, the program 200 may prompt interactions between participants. The program 200 can determine if the implemented modifications to the metaverse collaborative session are improving the attentiveness and engagement levels of a participant based on the utilized feedback loop. Additionally, in response to detecting that one or more participants are experiencing a loss of attentiveness and engagement due to eye fatigue, the program 200 can implement a virtual reality device break for the one or more participants. The program 200 can implement a VR device 114 break by pausing the metaverse collaborative session for a predetermined amount of time and instructing the participants to remove their VR devices 114 via a prompt on the GUI of the VR device 114.

Referring now to FIG. 3, a system diagram illustrating an exemplary program environment 300 of an implementation of a metaverse effectiveness boosting determination process 201 is depicted according to at least one embodiment. Here, the program 200 comprises a VR module 302 and an attentiveness boosting module 304. The exemplary program environment 300 details the interactions between the VR module 302 and the attentiveness boosting module 304. Additionally, the exemplary program environment 300 details the interactions between the VR module 302 and the peripheral device set 114, the eye strain module 304 and the peripheral device set 114, the attentiveness boosting module 304 and the wearable device set 123, and the metaverse effectiveness boosting determination program 200 and the database 130.

The VR module 302 may be used to create, manage, and display the virtual simulated environment and VR objects within the virtual simulated environment. The attentiveness boosting module 304 may be configured to determine a participant's real-time attentiveness and engagement levels, predict a participant's attentiveness and engagement threshold limits, monitor the attentiveness and engagement of a participant, segment participants in a metaverse collaborative session into groups, customize a metaverse collaborative session for a group of participants, create an attentiveness profile for a participant, analyze a participant's historical data, determine whether a participant's attentiveness and engagement requires boosting throughout a metaverse collaborative session, and dynamically modify a metaverse collaborative session and/or recommend a VR device 114 break to improve the attentiveness and engagement of participants.

It may be appreciated that FIGS. 2 through 3 provide only an illustration of one implementation and do not imply any limitations with regard to how different embodiments may be implemented. Many modifications to the depicted environments may be made based on design and implementation requirements.

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
receiving historical data for participants in a virtual collaborative session, wherein the historical data is collected during previous virtual collaborative sessions and comprises:
interactions of the participants with virtual content during the virtual collaborative sessions; and
eye image data collected by sensors worn by the participants during the virtual collaborative sessions;
creating attentiveness profiles for the participants based on the received historical data segmenting the participants into groups, wherein each of the groups includes at least two of the participants, and wherein the segmenting comprises clustering the attentiveness profiles of the participants based on information in the attentiveness profiles;
based on the clustered attentiveness profiles, generating versions of the virtual collaborative session respectively corresponding to the groups;
inserting the groups of participants into the respectively corresponding versions of the virtual collaborative session; and
dynamically customizing the versions of the virtual collaborative session during the virtual collaboration session, wherein the dynamically customizing comprises, for each group from the groups of participants:
continuously monitoring data indicating attentiveness of the participants in the group, wherein the data comprises, for each participant, a frequency of interactions during the virtual collaborative session and a predicted level of eye fatigue;
determining, based on the monitored data, that the attentiveness of at least one of the participants in the group is below a threshold level for the group; and
in response to the determining, dynamically modifying virtual content displayed to the participants in the group and prompting interactions between the participants in the group.

2. The method of claim 1, wherein:
the level of eye fatigue is predicted based on sensor data.

3. The method of claim 1, wherein the dynamically modifying comprises:
based on the predicted level of eye fatigue, instructing at least one of the participants in the group to take a virtual reality device break.

4. The method of claim 1, wherein the dynamically modifying comprises:
inserting one or more images and/or one or more sounds into the version of the virtual collaborative session displayed to the group.

5. The method of claim 1, wherein the historical data is collected using one or more virtual reality devices and one or more wearable devices.

6. The method of claim 1, wherein the inserting comprises:

displaying a virtual simulated environment on one or more virtual reality devices of the participants.

7. The method of claim 1, wherein creating the attentiveness profiles for the participants comprises:

predicting threshold levels of attentiveness and engagement for the participants using a trained machine learning model.

8. A computer system comprising:

one or more processors;

one or more computer-readable storage media; and program instructions stored on the one or more computer-readable storage media to cause the one or more processors to perform a method comprising:

receiving historical data for participants in a virtual collaborative session, wherein the historical data is collected during previous virtual collaborative sessions and comprises:

interactions of the participants with virtual content during the virtual collaborative sessions; and eye image data collected by sensors worn by the participants during the virtual collaborative sessions;

creating attentiveness profiles for the participants based on the received historical data segmenting the participants into groups, wherein each of the groups includes at least two of the participants, and wherein the segmenting comprises clustering the attentiveness profiles of the participants based on information in the attentiveness profiles;

based on the clustered attentiveness profiles, generating versions of the virtual collaborative session respectively corresponding to the groups;

inserting the groups of participants into the respectively corresponding versions of the virtual collaborative session; and dynamically customizing the versions of the virtual collaborative session during the virtual collaboration session, wherein the dynamically customizing comprises, for each group from the groups of participants:

continuously monitoring data indicating attentiveness of the participants in the group, wherein the data comprises, for each participant, a frequency of interactions during the virtual collaborative session and a predicted level of eye fatigue;

determining, based on the monitored data, that the attentiveness of at least one of the participants in the group is below a threshold level for the group; and in response to the determining, dynamically modifying virtual content displayed to the participants in the group and prompting interactions between the participants in the group.

9. The computer system of claim 8, wherein:

the level of eye fatigue is predicted based on sensor data.

10. The computer system of claim 8, wherein the dynamically modifying comprises:

based on the predicted level of eye fatigue, instructing at least one of the participants in the group to take a virtual reality device break.

11. The computer system of claim 8, wherein the dynamically modifying comprises:

inserting one or more images and/or one or more sounds into the customized version of the virtual collaborative session for the group.

12. The computer system of claim 8, wherein the historical data is collected using one or more virtual reality devices and one or more wearable devices.

13. The computer system of claim 8, wherein the inserting comprises:

displaying a virtual simulated environment on one or more virtual reality devices of the participants.

14. The computer system of claim 8, wherein creating the attentiveness profiles for the participants comprises:

predicting threshold levels of attentiveness and engagement for each of the participants using a trained machine learning model.

15. A computer program product comprising:

one or more computer-readable storage media; and program instructions stored on the computer-readable storage media, the program instructions executable by a processor to cause the processor to perform a method comprising:

receiving historical data for participants in a virtual collaborative session, wherein the historical data is collected during previous virtual collaborative sessions and comprises:

interactions of the participants with virtual content during the virtual collaborative sessions; and eye image data collected by sensors worn by the participants during the virtual collaborative sessions;

creating attentiveness profiles for the participants based on the received historical data;

segmenting the participants into groups, wherein each of the groups includes at least two of the participants, and wherein the segmenting comprises clustering the attentiveness profiles of the participants based on information in the attentiveness profiles;

based on the clustered attentiveness profiles, generating versions of the virtual collaborative session respectively corresponding to the groups;

inserting the groups of participants into the respectively corresponding versions of the virtual collaborative session; and dynamically customizing the versions of the virtual collaborative session during the virtual collaboration session, wherein the dynamically customizing comprises, for each group from the groups of participants:

continuously monitoring data indicating attentiveness of the participants in the group, wherein the data comprises, for each participant, a frequency of interactions during the virtual collaborative session and a predicted level of eye fatigue;

determining, based on the monitored data, that the attentiveness of at least one of the participants in the group is below a threshold level for the group; and in response to the determining, dynamically modifying virtual content displayed to the participants in the group and prompting interactions between the participants in the group.

16. The computer program product of claim 15, wherein:

the level of eye fatigue is predicted based on sensor data.

17. The computer program product of claim 15, wherein the dynamically modifying comprises:

based on the predicted level of eye fatigue, instructing at least one of the participants in the group to take a virtual reality device break.

18. The computer program product of claim 15, wherein the dynamically modifying comprises:

inserting one or more images and/or one or more sounds into the version of the virtual collaborative session displayed to the participants in the group.

19. The computer program product of claim 15, wherein the historical data is collected using one or more virtual reality devices and one or more wearable devices.

20. The computer program product of claim 15, wherein the inserting comprises:

displaying a virtual simulated environment on one or more virtual reality devices of the participants.

* * * * *